(12) United States Patent
Farrell et al.

(10) Patent No.: US 11,707,593 B2
(45) Date of Patent: Jul. 25, 2023

(54) SEDATION DEVICE

(71) Applicant: Sedana Medical Limited, Naas (IE)

(72) Inventors: Ron Farrell, Naas (IE); Pauric Carey, Carbury (IE)

(73) Assignee: Sedana Medical Limited, Naas (IE)

( * ) Notice: Subject to any disclaimer, the term of this patent is extended or adjusted under 35 U.S.C. 154(b) by 376 days.

(21) Appl. No.: 16/311,305

(22) PCT Filed: Jun. 21, 2017

(86) PCT No.: PCT/EP2017/065318
§ 371 (c)(1),
(2) Date: Dec. 19, 2018

(87) PCT Pub. No.: WO2017/220698
PCT Pub. Date: Dec. 28, 2017

(65) Prior Publication Data
US 2019/0201655 A1 Jul. 4, 2019

(30) Foreign Application Priority Data
Jun. 21, 2016 (EP) .................................. 16175577.2

(51) Int. Cl.
*A61M 16/18* (2006.01)
*A61M 16/14* (2006.01)
(Continued)

(52) U.S. Cl.
CPC .......... *A61M 16/18* (2013.01); *A61M 16/009* (2013.01); *A61M 16/085* (2014.02);
(Continued)

(58) Field of Classification Search
CPC ................ A61M 16/18; A61M 16/009; A61M 16/0093; A61M 16/085; A61M 16/106;
(Continued)

(56) References Cited

U.S. PATENT DOCUMENTS 4,115,277 A * 9/1978 Swank ................ A61M 1/3627
210/436
4,422,939 A 12/1983 Sharp et al.
(Continued)

FOREIGN PATENT DOCUMENTS

EP 0965372 A2 12/1999
EP 0972534 A2 1/2000
(Continued)

OTHER PUBLICATIONS

Secur2005, (Jun. 17, 2007), "Sedana", https://www.youtube.com/watch?v=R0syXscHD94 (Year: 2007).*
(Continued)

*Primary Examiner* — Timothy A Stanis
*Assistant Examiner* — Matthew R Moon
(74) *Attorney, Agent, or Firm* — Michael Crilly, Esquire

(57) ABSTRACT

A sedation device has a housing divided internally into a ventilator chamber and an associated evaporator chamber which overlap and are separated by a filter mounted between the chambers and forming a common gas-permeable dividing wall between the chambers. An inlet port is provided at one end of the ventilator chamber at a top of the housing for connection to a patient ventilator in use. An outlet port on the evaporator chamber can be connected via a breathing tube to a patient. An evaporator is mounted within the evaporator chamber for delivery of a volatile sedative into the evaporator chamber during use.

18 Claims, 11 Drawing Sheets

(51) Int. Cl.
*A61M 16/00* (2006.01)
*A61M 16/08* (2006.01)
*A61M 16/10* (2006.01)

(52) U.S. Cl.
CPC ........ *A61M 16/106* (2014.02); *A61M 16/142* (2014.02); *A61M 16/147* (2014.02); *A61M 2205/7509* (2013.01); *A61M 2205/7518* (2013.01)

(58) Field of Classification Search
CPC .............. A61M 16/142; A61M 16/147; A61M 2205/7509; A61M 2205/7518; A61M 16/101; A61M 16/01; A61M 16/104; A61M 16/105
See application file for complete search history.

(56) References Cited

U.S. PATENT DOCUMENTS

| | | | |
|---|---|---|---|
| 4,693,853 | A | 9/1987 | Falb et al. |
| 5,044,361 | A | 9/1991 | Werner et al. |
| 5,337,739 | A | 8/1994 | Lehman |
| 5,460,172 | A | 10/1995 | Eckerbom et al. |
| 5,468,451 | A | 11/1995 | Gedeon |
| 5,970,210 | A * | 10/1999 | Anthony ............. A61M 16/142 392/386 |
| 6,152,133 | A | 11/2000 | Psaros et al. |
| 6,155,255 | A | 12/2000 | Lambert |
| 6,168,718 | B1 | 1/2001 | Sutter et al. |
| 6,206,002 | B1 | 3/2001 | Lambert |
| 6,275,650 | B1 | 8/2001 | Lambert |
| 6,363,930 | B1 | 4/2002 | Clawson et al. |
| 6,488,028 | B1 | 12/2002 | Lambert |
| 7,841,339 | B2 | 11/2010 | Lambert |
| 8,485,187 | B2 | 7/2013 | Orr et al. |
| 2005/0166917 | A1 | 8/2005 | Ahlmen et al. |
| 2007/0079827 | A1 | 4/2007 | Lambert |
| 2009/0050148 | A1 | 2/2009 | Heinonen et al. |
| 2009/0301475 | A1 * | 12/2009 | Korneff ............... A61M 16/106 128/201.13 |
| 2010/0212668 | A1 | 8/2010 | Flanagan et al. |
| 2010/0269828 | A1 | 10/2010 | Orr et al. |
| 2017/0319811 | A1 * | 11/2017 | Foote ........................ F24F 6/10 |

FOREIGN PATENT DOCUMENTS

| | | |
|---|---|---|
| EP | 1613383 B1 | 10/2008 |
| EP | 1778324 B1 | 10/2009 |
| WO | 88/07876 A1 | 10/1988 |
| WO | 97/14465 A1 | 4/1997 |
| WO | 97/36628 A1 | 10/1997 |
| WO | 98/20926 A1 | 5/1998 |
| WO | 99/33523 A1 | 7/1999 |
| WO | 00/02610 A1 | 1/2000 |
| WO | 00/21595 A1 | 4/2000 |
| WO | 2004/087244 A1 | 10/2004 |
| WO | 2004087244 A1 | 10/2004 |
| WO | 2004/098688 A1 | 11/2004 |
| WO | 2005/037357 A1 | 4/2005 |
| WO | 2010/096299 A1 | 8/2010 |

OTHER PUBLICATIONS

Berton, Jerome MD; Sargentini, Cyril MD; Nguyen, Jean-Luc MD; Belii, Adrian MD; and Beydon, Laurent; AnaConDa Reflection Filter: Bench and Patient Evaluation of Safety and Volatile Anesthetic Conservation, Anesthesia & Analgesia: Jan. 2007—vol. 104—Issue 1—p. 130-134 doi: 10.1213/01.ane.0000248221.44383.43.
International Search Report for PCT/EP2017/075014 by the European Patent Office; dated Nov. 29, 2017; 5 pages.
Written Opinion for PCT/EP2017/075014 by the European Patent Office; 6 pages, dated Nov. 29, 2017.
International Search Report for PCT/EP2017/065318 by the European Patent Office, dated Aug. 8, 2017, 3 pages.
Written Opinion for PCT/EP2017/065318 by the European Patent Office, 5 pages, dated Aug. 8, 2017.

* cited by examiner

SEDATION DEVICE

CROSS REFERENCE TO RELATED APPLICATIONS

This application is a national phase to PCT Application No. PCT/EP2017/065318 filed Jun. 21, 2017, which in turn claims priority to European Patent Application No. EP16175577.2 filed Jun. 21, 2016, both applications being incorporated in their entirety herein by reference thereto.

FEDERALLY SPONSORED RESEARCH AND DEVELOPMENT

None.

BACKGROUND OF THE INVENTION

1. Field of the Invention

This invention relates to a sedation device and in particular to a sedation device for sedative delivery capable of handling a sedative in volatile gas form.

2. Background

Volatile anaesthetics are potent drugs documented for use in general anaesthesia. General anaesthesia is the induction of a state of unconsciousness with the absence of pain sensation over the entire body through the administration of either Volatile or Intravenous anaesthetic drugs. An anaesthesia machine is normally required for the administration of the volatile anaesthetic. The development of anaesthesia machines was heavily focused on the need to minimise the consumption of the expensive volatile agent in order to reduce costs and minimise the negative effect of waste gas on the environment. Anaesthesia machines function on the principal of a circle system in which they re-circulate used gas through a carbon dioxide absorber before returning it to the patient. Thus, after the initial input, very little new anaesthetic gas is needed to maintain the desired level of anaesthesia.

Anaesthesia machines require a high capital investment along with significant on-going running costs, which can put pressure on hospital budgets. Furthermore modern anaesthesia machines necessitate specially trained personnel to ensure the equipment and the carbon dioxide absorber are set up and operating correctly.

In order to reduce health care costs, increasing number of patients are undergoing surgery in outpatient or ambulatory settings i.e. surgery that does not require an overnight stay in a hospital and which is typically run by individuals or small partnerships. The high capital costs and technical support required for anaesthesia machines is prohibitive for such small operators and thus makes it difficult to use volatile anaesthetics for such applications.

In Intensive Care Units (ICU's), mechanically ventilated patients have traditionally been sedated using intravenous drugs to achieve the required level of sedation and pain relief. Many doctors would prefer to use volatile sedatives in the ICU because it has many benefits over the use of intravenous drugs, particularly for certain patient indications. The use of volatile sedative agents in the ICU as an alternative sedation method for mechanically ventilated patients has been the subject of clinical research for almost 30 years. The results of such show that volatile sedatives have many benefits over conventional drugs but, since there was no convenient and efficient method of delivery, the use of volatiles never gained momentum.

The use of anaesthesia machines in the ICU is prohibitive due to their high capital cost, and the need for specially trained personnel. In addition, the ventilator component associated with anaesthesia machines does not have the appropriate functionality for use with intensive care patients. The alternative to the anaesthesia machine is an open flow system, which uses a large amount of expensive anaesthetic, exhausting the waste directly into the atmosphere.

WO 97/14465 discloses a sedation device for supplying a sedative to a patient with an absorption filter for absorption and desorption of sedative during use. The device includes a housing for mounting in an airflow path between a respirator and a patient. An evaporator located within the housing releases sedative into the airstream delivered through the device between the respirator and the patient. An absorption filter is mounted within the housing to absorb excess sedative exhaled by the patient and release the recovered sedative back into the airstream when the patient takes the next breath in order to conserve sedative. The filter can be moved within the housing in use between a position in which the airstream fully passes through the filter and a position in which the airstream bypasses the filter.

Various other devices for recovering sedative during the administration of an inhaled sedative are disclosed in WO 97/36628, WO 98/20926, WO 05/037357, EP 0972534, WO 88/07876, and US 2009/0050148.

The insertion of any device between the patient and the Y-piece of the breathing circuit connected to the ventilator presents two significant complications to respiration for the patient, namely increased dead-space and pressure drop across the device. The device increases the overall volume of carbon dioxide laden air that needs to be cleared with each breathing cycle which is referred to as dead-space. Any device inserted into the breathing tube adds to this dead-space and increases the amount of carbon dioxide a patient will inhale with each breath. If the volume of air inhaled and exhaled by the patient, termed the tidal volume, does not sufficiently exceed the dead-space the patient cannot clear enough carbon dioxide from the ventilation circuit and the concentration of carbon dioxide rises within the air stream and eventually in the blood. This leads to a state of respiratory and metabolic distress. In patients with relatively large tidal volumes clearance of carbon dioxide from such devices does not usually present any difficulty. However for patients with smaller tidal volumes, such as smaller adults, patients with reduced lung function and children, sufficient clearance of carbon dioxide may be difficult to achieve without implementing aggressive ventilation. For such patients it would be desirable to reduce the dead-space by minimising the volume of the sedation device. In general, it could be said that patients in an intensive care department are seriously ill and it is always beneficial to reduce the dead space and thereby reduce the resistance to breath.

Simply down-sizing existing devices does not provide a solution to this problem as it leads to an unacceptable pressure drop across the device in use. Even a small pressure drop can make respiration very difficult for some patients. The pressure drop is often at its greatest when peak air flow is needed by the patient, that is when the patient needs most air the device is most resistant to air flow. The reflection efficiency of the carbon filter may also be reduced and thus a greater amount of sedative will be required which is undesirable.

The present invention is directed towards overcoming these problems.

SUMMARY OF THE INVENTION

According to the invention there is provided a sedation device, including: a housing having an internal volume of between 30 ml and 110 ml; the housing having a ventilator chamber and an associated juxtaposed evaporator chamber communicating with the ventilator chamber; a filter mounted between the ventilator chamber and the evaporator chamber forming a common gas-permeable dividing wall between the ventilator chamber and the evaporator chamber; the ventilator chamber having an inlet port for connection to a ventilator; the evaporator chamber having an outlet port for connection to a patient breathing tube; and an evaporator mounted within the evaporator chamber.

In a particularly preferred embodiment, the inlet port is mounted at a side of the ventilation chamber and is positioned to direct air across a surface of the filter in the ventilator chamber, and there is provided a deflector ramp mounted within the ventilator chamber, the deflector ramp associated with and adjacent the inlet port, the deflector ramp extending across the inlet port and spaced-apart therefrom, the deflector ramp being angled relative to the inlet port and flaring outwardly away from the inlet port to direct incoming air from the inlet port inwardly from the inlet port towards the filter and outwardly from the inlet port across a surface of the filter.

In another embodiment, an elongate air distribution fin is mounted within the ventilator chamber on an outer wall of the ventilator chamber in alignment with the inlet port at an inner end of the ramp and extending away from the ramp.

In another embodiment, the evaporator chamber has a concave outer wall portion forming an elongate channel within which the evaporator is mounted, the evaporator comprising an elongate porous rod, evaporator mounting supports within the evaporator chamber supporting the evaporator rod within the elongate channel spaced-apart from the concave outer wall portion and in alignment with the outlet port of the evaporator chamber.

In one embodiment of the invention, an air distribution manifold is mounted at the inlet port for directing incoming air across a surface of the filter.

In another embodiment, a curved ramp is provided at an outlet of the air distribution manifold for directing incoming air across the filter.

In another embodiment, the inlet port is mounted at a side of the ventilator chamber and is positioned to direct air across a surface of the filter in the ventilator chamber.

In another embodiment, the outlet port is mounted at a side of the evaporator chamber and the outlet port is positioned to draw air across a surface of the filter in the evaporator chamber.

In another embodiment, the inlet port and the outlet port are substantially parallel, that is the axes of the inlet port and outlet port are substantially parallel, and the inlet port and outlet port are located at opposite ends of the housing.

In another embodiment, the air distribution manifold extends for between 20% and 35% of the length of the ventilator chamber.

In another embodiment, the air distribution manifold extends for about 25% of the length of the ventilator chamber.

In another embodiment, a width of an outlet end of the air distribution manifold is between 50% and 75% of the maximum width of the ventilator chamber.

In another embodiment, the width of the outlet end of the air distribution manifold is about 65% of the maximum width of the ventilator chamber.

In another embodiment, the ventilator chamber flares outwardly of the air distribution manifold.

In another embodiment, the evaporator chamber has a concave or bowl-like profile.

In another embodiment, the evaporator chamber has a side wall extending outwardly from the filter with the concave outer wall portion at an outer end of the side wall.

In another embodiment, the side wall is tapered between opposite ends of the evaporator chamber, the outlet port being mounted at a wider end of the evaporator chamber.

In another embodiment, the evaporator mounting supports are provided at opposite ends of the evaporator chamber.

In another embodiment, one of said evaporator mounting supports is mounted at the outlet port.

In another embodiment, one or more filter support posts are mounted within the evaporator chamber and located between the mounting supports, the filter support posts projecting outwardly from the concave outer wall portion.

In another embodiment, a filter retaining grille is mounted in the ventilator chamber against the surface of the filter, and at least one spacer element extends outwardly from an outer wall of the ventilator chamber to engage the grille and urge the grille away from the outer wall and against the surface of the filter.

In another embodiment, the spacer element comprises a plurality of spaced-apart spacer posts.

In another embodiment, each spacer post has a pointed leading edge facing the inlet port.

In another embodiment, the air distribution fin has a pointed leading edge facing the inlet port.

In another embodiment, the housing is ovoid. Alternatively, the housing may be elliptical or circular.

In another embodiment, the inlet port is located at a narrow end of the housing and the outlet port is located at a wide end of the housing.

In another embodiment, inner surfaces of the housing are smooth or highly polished.

In another embodiment the housing has an internal volume of about 50 ml.

BRIEF DESCRIPTION OF THE DRAWINGS

The invention will be more clearly understood by the following description of some embodiments thereof, given by way of example only, with reference to the accompanying drawings.

DETAILED DESCRIPTION OF THE INVENTION

Figure 1:
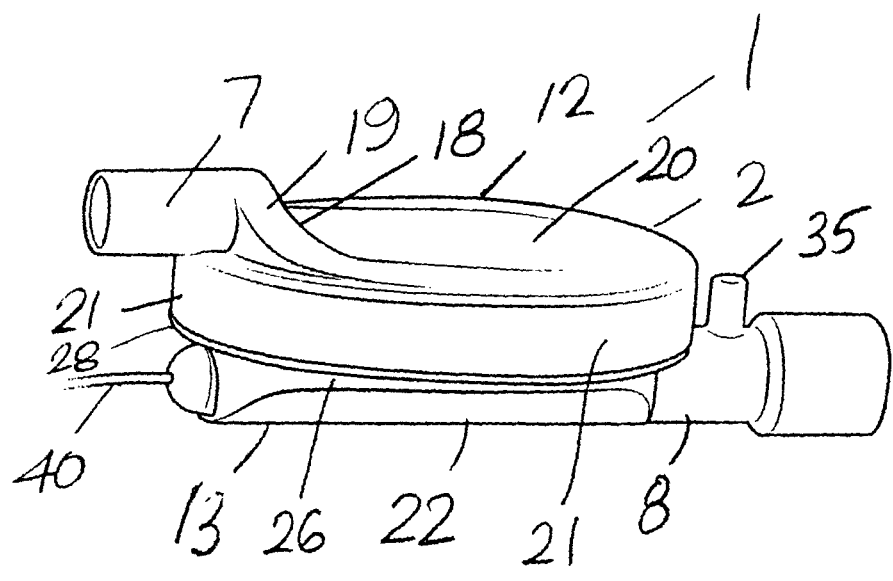
FIG. 1 is a perspective view of a sedation device according to the invention.

Referring to the drawings and initially to FIGS. 1 to 9 thereof, there is illustrated a sedation device according to the invention indicated generally by the reference numeral 1 for anaesthetic delivery and recycling. The sedation device 1 has a housing 2 within which is provided a ventilator chamber 3 and an associated evaporator chamber 4 which overlap and are separated by a filter 5 mounted between said chambers 3, 4 and forming a common gas-permeable dividing wall between the chambers 3, 4. An inlet port 7 is provided at one end of the ventilator chamber 3 at a top of the housing 2 for connection to a patient ventilator 50 (FIG. 9) in use. An outlet port 8 on the evaporator chamber 4 can be connected via a breathing tube 54 to a patient. It will be noted that in this case the inlet port 7 and outlet port 8 are substantially parallel and located at opposite ends of the housing 2 along a longitudinal centre line of the housing 2. An evaporator 10 is mounted within the evaporator chamber 4 for delivery of a volatile sedative into the evaporator chamber 4 during use.

Figure 3:
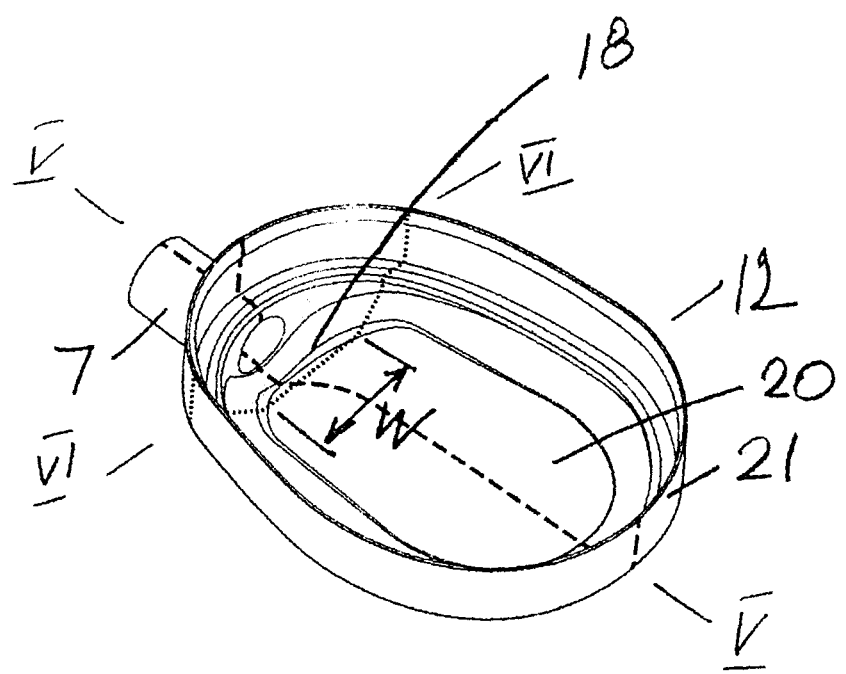
FIG. 3 is a perspective view of a ventilator chamber housing forming portion of the device.
Figure 4:
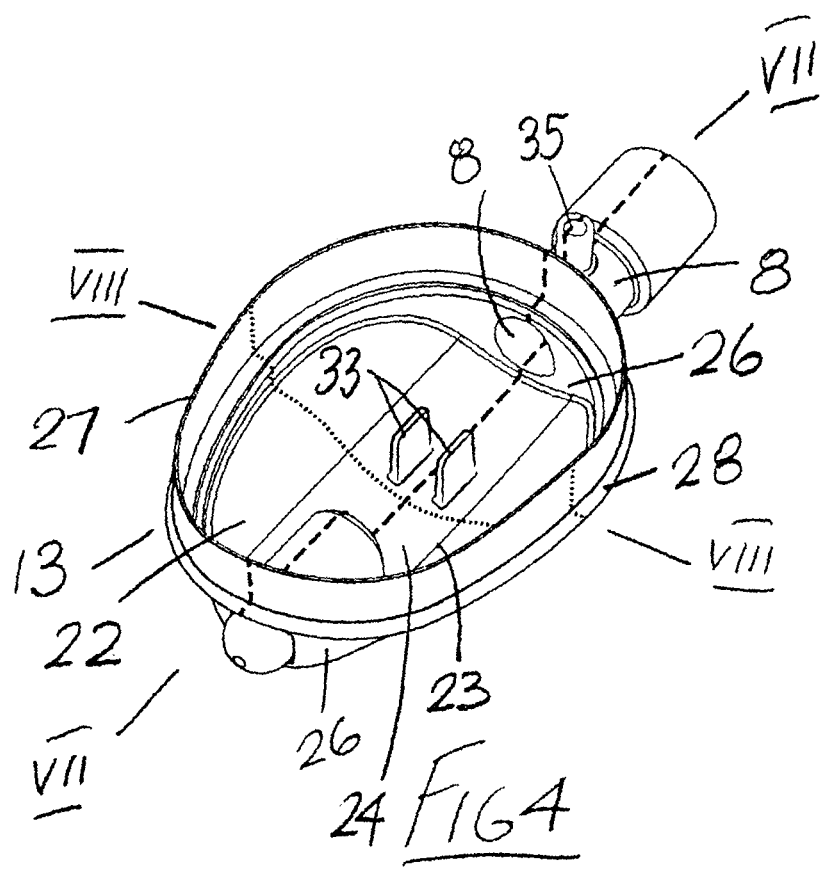
FIG. 4 is a perspective view of an evaporator chamber housing forming portion of the device.

The housing 2 has an internal volume of between 30 ml and 110 ml and may conveniently be made of plastics material and is provided in two parts which snap together, namely a ventilator chamber housing 12 and an evaporator chamber housing 13. The housing 2 is generally ovoid as best seen in FIG. 3 and FIG. 4, although other shapes such as elliptical or circular may also be possible. It will be noted that the inlet port 7 is located at a narrow end of the housing 2 and the outlet port 8 is mounted at a wide end of the housing 2.

Figure 2:
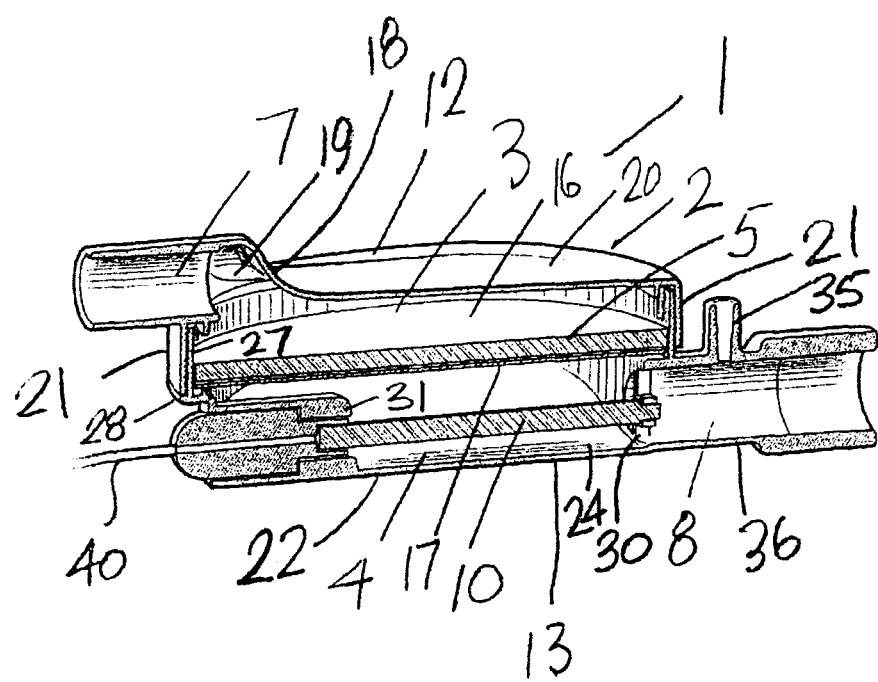
FIG. 2 is a sectional perspective view of the sedation device.

Referring in particular to FIG. 2 and FIG. 3 an air deflector ramp 18 is mounted within the ventilator chamber 3 at the inlet port 7 for directing incoming air across an upper surface 16 of the filter 5. The air deflector ramp 18 is associated with and mounted adjacent the inlet port 7, extending across the inlet port 7 and spaced-apart therefrom. The air deflector ramp 18 is angled relative to the inlet port 7, as shown in FIG. 2, extending downwardly and away from a top of the inlet port 7 and flaring outwardly away from the inlet port 7 at each side 19 of the ramp 18 to direct incoming air from the inlet port 7 inwardly towards the filter 5 and outwardly from the inlet port 7 across a whole of the upper surface 16 of the filter 5. That is incoming air delivered from the ventilator through the inlet port 7 is directed downwardly and outwardly from the inlet port 7 and distributed across the upper surface 16 of the filter 5.

This air deflector ramp 18 extends for between 20% and 35% of the overall length of the ventilator chamber 3 and preferably extends for about 25% of the length of the ventilator chamber 3. A width W (FIG. 3) of an outlet end of the air deflector ramp 18 is preferably between 50% and 75% of the maximum width of the ventilator chamber 3.

It will also be noted that the air deflector ramp 18 is curved to provide a smooth distribution of air throughout the ventilator chamber 3. The air deflector ramp 18 promotes inflowing air to spread out and move over the inside surface of the ventilation chamber 3. Air is distributed evenly throughout the ventilation chamber 3 and across the upper surface 16 of the filter 5.

Figure 5:
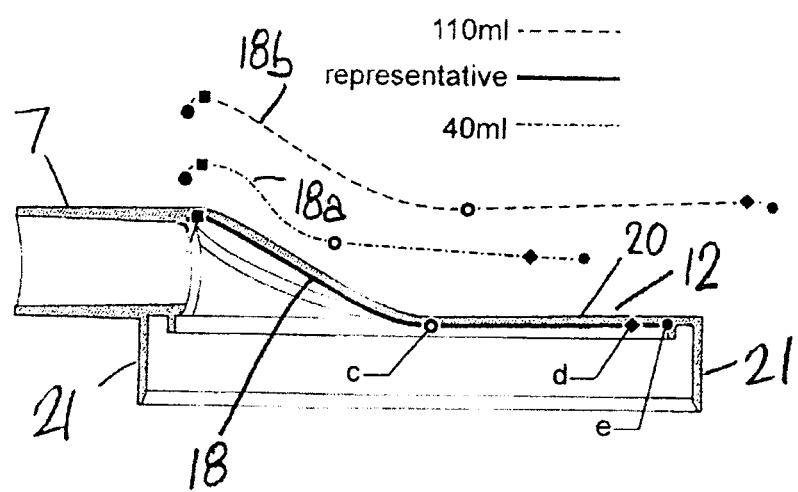
FIG. 5 is a sectional elevational view taken along the line V-V of FIG. 3.
Figure 6:
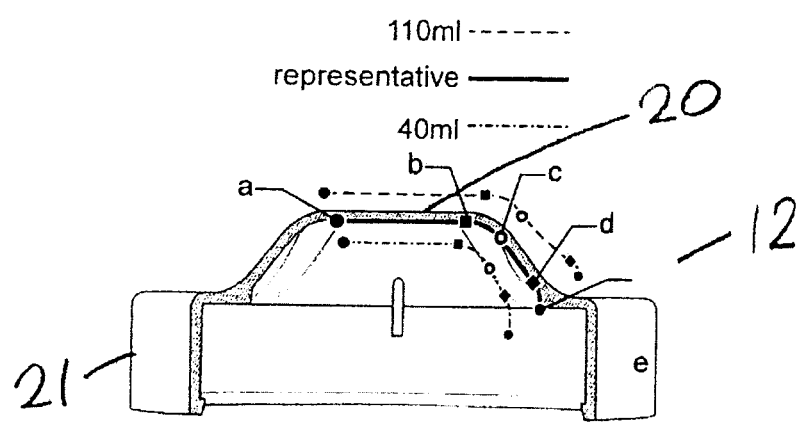
FIG. 6 is a sectional elevational view taken along the line VI-VI of FIG. 3.
Figure 7:
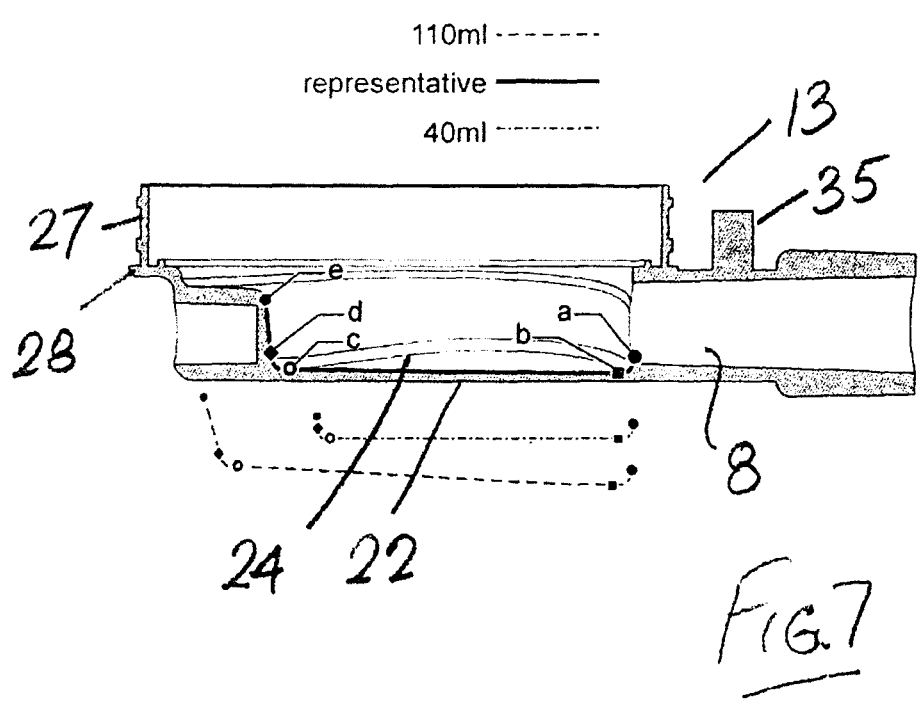
FIG. 7 is a sectional elevational view taken along the line VII-VII of FIG. 4.

To provide a smooth flow of air through the sedation device 1 the shape of the curved ramp 18 will vary depending on the internal volume of the housing 2. Generally speaking, the curvature of the ramp 18 is inversely proportional to the internal volume. That is as the internal volume is reduced ramp curvature becomes more pronounced. FIG. 5 shows a ramp 18 of mean curvature, and also illustrates a more pronounced ramp curvature 18a for a 40 ml volume housing 2 and a shallower ramp curvature 18b for a 110 ml volume housing 2.

Further, the ventilator chamber 3 flares outwardly of the air deflector ramp 18. It will be appreciated that the arrangement of the air deflector ramp 18 and the shape of the ventilation chamber 3 is such as to promote an even and smooth delivery of air delivered in through the inlet port 7 across the upper surface 16 of the filter 5.

The ventilator chamber housing 12 has a top wall 20 with a downwardly depending peripheral skirt 21 for complementary inter-engagement with the ventilator chamber housing 13. Suitable formations are provided on an inside face of the skirt 21 for snap engagement with complementary formations on the ventilator chamber housing 13 to releasably secure the two chamber housings 12, 13 together. Alternatively, the housing parts 12, 13 could be secured together in some other fashion such as by gluing or welding for example.

Referring now in particular to FIG. 2 and FIG. 4, the evaporator chamber housing 13 is also of plastics material and comprises a bowl-like bottom wall 22 with a concave outer wall portion 23 forming an elongate central channel 24 in alignment with the outlet port 8 of the evaporator chamber 4 within which the evaporator 10 is mounted. An upstanding side wall 26 extends around a periphery of the bottom wall 22. At a top of the side wall 26 an upstanding peripheral skirt 27 cooperates with the associated skirt 21 on the ventilator chamber housing 12 to secure the two housing chambers 12, 13 together. A bottom edge of the skirt 21 seats against a laterally projecting flange or lip 28 at the bottom of the skirt 27. The flange 28 may optionally incorporate a valley for gluing. It will be noted that the side wall 26 is tapered between opposite ends of the evaporator chamber 4, and the outlet port 8 is mounted on the side wall 26 at a wider end of the evaporator chamber 4.

Figure 8:
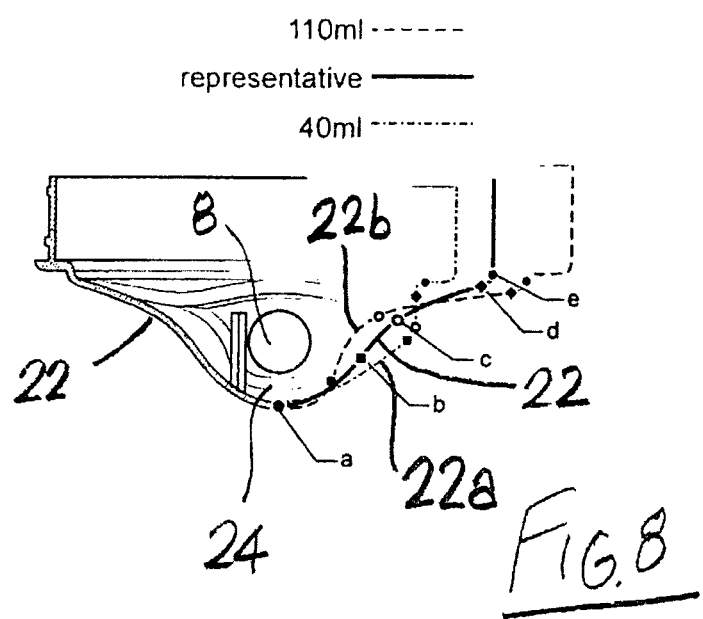
FIG. 8 is a sectional elevational view taken along the line VIII-VIII of FIG. 4.

The central channel 24 in the bottom wall 22 forming the floor of the evaporator chamber 4 is curved to direct air around the evaporator 10 which is held spaced-apart from the side wall of the central channel 24 by the evaporator mounting supports 30, 31. The bottom wall 22 concavity is looser and more open at small internal volumes while tighter and more acute at larger internal volumes. FIG. 8 illustrates a bottom wall 22 of mean curvature, the looser curvature of a bottom wall 22a for a 40 ml volume housing 2 and the tighter curvature of a bottom wall 22b for a 110 ml volume housing 2.

The evaporator mounting supports 30, 31 are provided at opposite ends of the evaporator chamber 4 and comprise a first mounting support 30 mounted at the outlet port 8 and a second mounting support 31 mounted at the side wall 26 at the opposite end of the evaporator chamber 4. A pair of spaced-apart filter support posts 33 is located between the mounting supports 30, 31 projecting outwardly from the bottom wall 22, in the channel 24. These filter support posts 33 may have a rectangular section or more preferably a round or elliptical section aligned with a longitudinal axis of the evaporator chamber 4 to minimise turbulence in air flowing through the evaporator chamber 4.

A sampling port 35 projects radially outwardly of a tube 36 forming the outlet port 8. In use this can be connected by a sampling line 37 to a gas monitor 38 (FIG. 9) so that the concentration of volatile sedative can be measured and used to control the addition of new sedative through the evaporator 10 into the evaporator chamber 4.

The evaporator 10 comprises an elongate porous polymer rod extending between the mounting supports 30, 31. Various other types of evaporator might alternatively be provided such as a heated or vibrating element. A sedative delivery line 40 connects the evaporator 10 to a sedative reservoir 41 (FIG. 9) with a syringe or pump. Sedative from the reservoir 41 is vaporised by the evaporator 10 and combines with air within the evaporator chamber 4 prior to delivery through the outlet port 8 to a patient. Any suitable means, such as the syringe or pump or other delivery means can be provided for delivering the sedative material from the reservoir 41 to the evaporator 10.

The filter 5 comprises an absorbent carbon felt filter bonded or not bonded to an anti-microbial and anti-viral filter. The carbon felt filter is able to absorb the volatile sedative during expiration and remit it during inspiration, thus it is able to recycle the sedative. The carbon felt is capable of reflecting the expired volatile agent at the most common ventilator parameters without reflecting any clinically significant concentration of carbon dioxide. The carbon felt also reflects heat and moisture.

It will be noted that the filter 5 is substantially parallel to central axes of the inlet port 7 and outlet port 8 so that air flowing into or out of the sedation device 1 flows across the top surface 16 and bottom surface 17 of the filter 5. The activated carbon on the filter 5 functions to reflect heat, moisture and volatile sedative back to the patient. The anti-bacterial and anti-viral filter serves to protect the ventilator circuit from pathogenic contamination.

Figure 9:
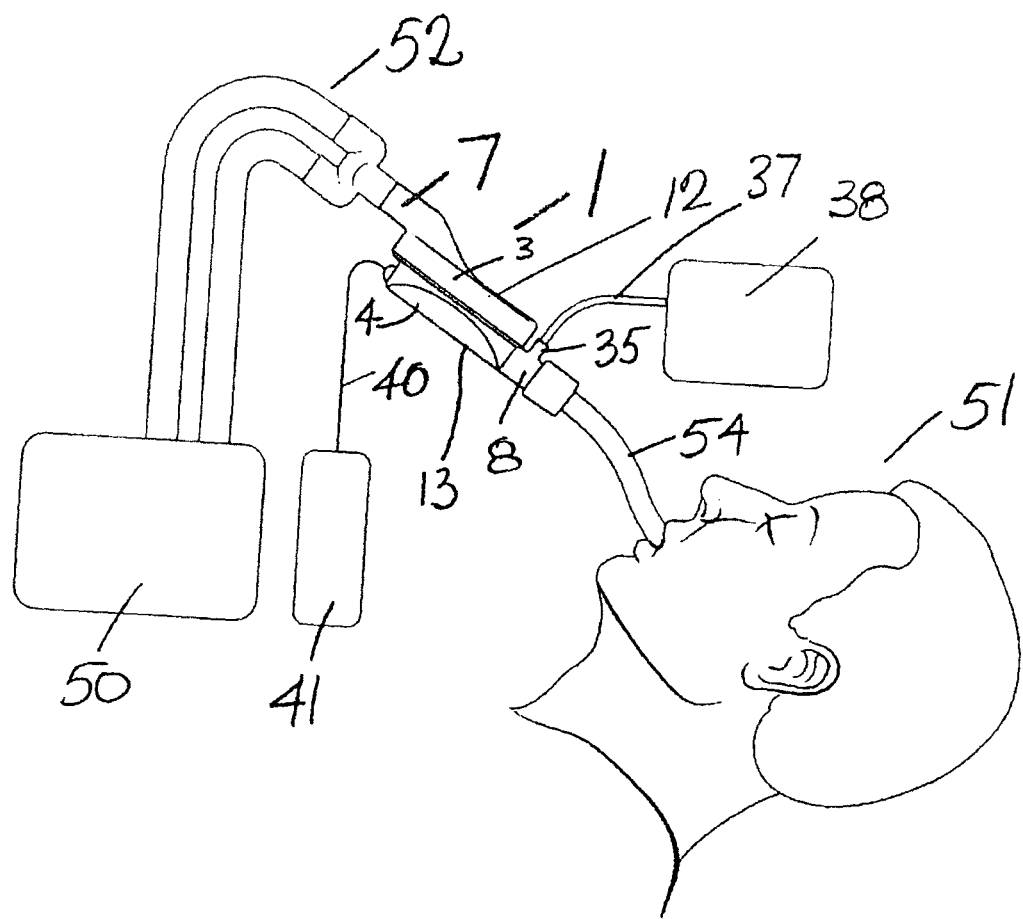
FIG. 9 is an elevational view showing the sedation device in use.

FIG. 9 shows the sedation device 1 in use mounted between a ventilator 50 and a patient 51. The inlet port 7 of the sedation device 1 connects via tubing 52 with the ventilator 50. The outlet port 8 connects via a breathing tube 54 with the patient 51. Fresh air delivered from the ventilator 50 enters the ventilator chamber 3 through the inlet 7. Incoming air transitions from a narrow tubular air stream delivered through the inlet port 7 into a wide flat air stream flowing smoothly across the ventilator chamber 3. Air is evenly distributed throughout the ventilator chamber 3 and across the upper surface 16 of the filter 5. The air flows through the filter 5 into the evaporator chamber 4. Volatile sedative injected into the evaporator 10 mixes with the fresh air before exiting the evaporator chamber 4 through the outlet port 8 for delivery through the breathing tube 54 to the patient 51.

A small sample of the air is extracted through the sample port 35 for measurement by the external gas monitor 38. The concentration of sedative measured by the external gas monitor 38 can be used to inform the rate at which new sedative is pumped into the evaporator chamber 4 to supplement the recycled sedative. Air exhaled by the patient 51 mixed with any excess sedative gas, re-enters the evaporator chamber 4. This air/sedative mixture travels up through the filter 5 where the sedative is absorbed and the exhaled air is exhausted out of the device. Upon subsequent inhalations, the fresh air pulls the recovered sedative from the filter 5 as it passes through the filter 5 from the ventilator chamber 3 into the evaporator chamber 4 and re-uses it as the patient breathes, thereby reflecting and conserving sedative.

Figure 10:
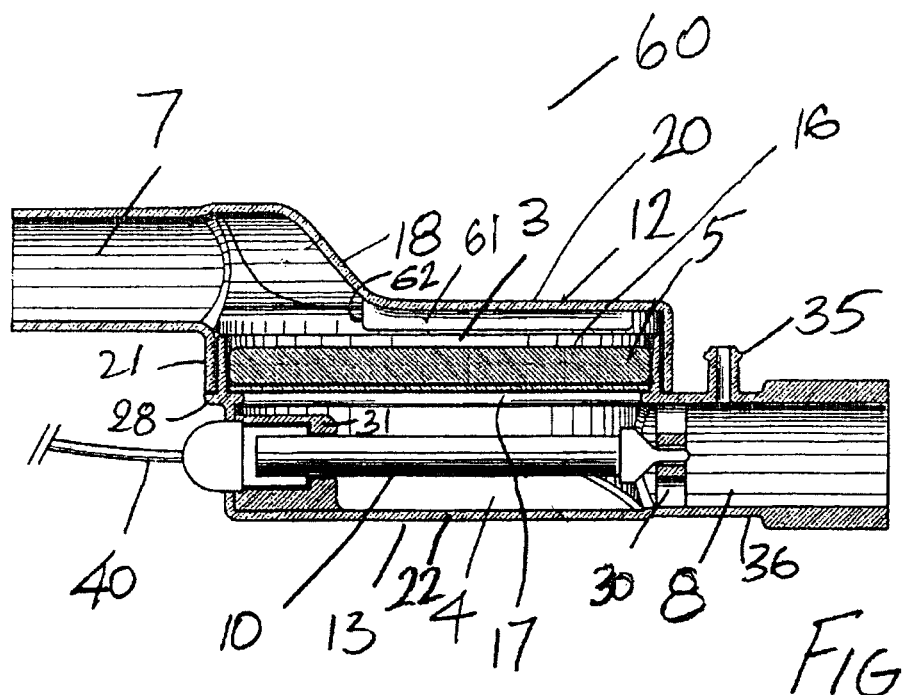
FIG. 10 is a sectional elevational view of another sedation device according to a second embodiment of the invention.

Referring now to FIG. 10, there is shown another sedation device according to the invention, indicated generally by the reference numeral 60. This is largely similar to the sedation device described previously and like parts are assigned the same reference numerals. In this case an elongate air distribution fin 61 is mounted within the ventilator chamber 3 on an inside face of the outer or top wall 20 of the ventilator chamber housing 12. The fin 61 is perpendicular to the top wall 20 and is centrally located on the top wall 20 in alignment with the inlet port 7 at an inner end of the ramp 18 and extending away from the ramp 18. The fin 61 has a pointed leading edge 62 facing the inlet port 7. The fin 61 aids in promoting an even distribution of incoming air across the surface 16 of the filter 5.

Figure 11:
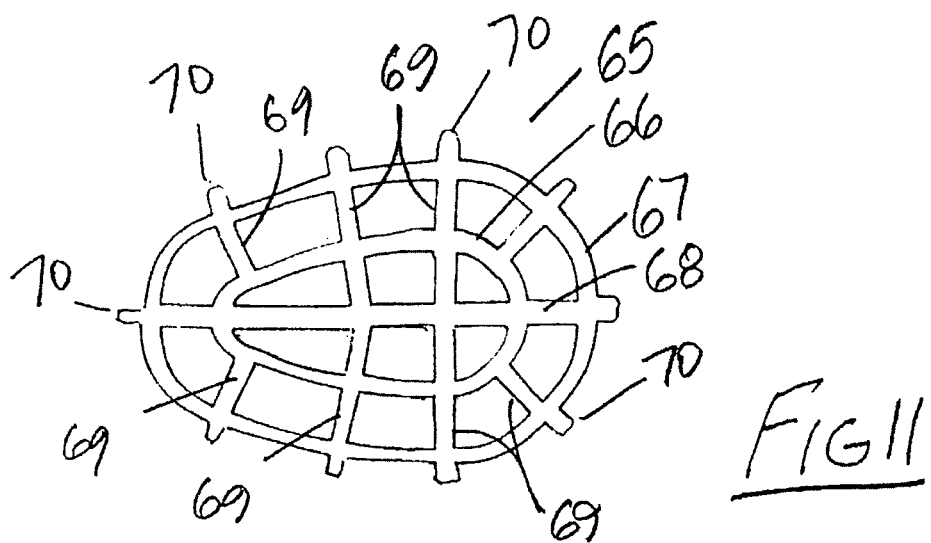
FIG. 11 is a perspective view of a filter retaining grille for use with sedation devices of the invention.

Referring now to FIG. 11, there is illustrated a filter retaining grille indicated generally by the reference numeral 65 for use with the sedation devices of the invention. The grille 65 has a pair of spaced-apart concentric ovoid rings, namely an inner ring 66 and an outer ring 67 mounted on a axial spine 68 with outwardly extending spaced-apart arms 69 arranged thereon which project outwardly of the outer ring 67. With reference to FIG. 10, the grille 65 is mounted within the ventilator chamber 3 against an upper surface 16 of the filter 5 with outer ends 70 of each arm 69 and the spine 68 engaging against an inner face of the upstanding skirt 27 of the evaporator chamber 4. The fin 61 engages against the central axial spine 68 to urge the grille 65 against the upper surface 16 of the filter 5 to maintain an airflow space above the filter 5, that is to keep the filter 5 spaced away from the outer or top wall 20 of the ventilator chamber 3. Thus, the fin 61 in this case also functions as a spacer element for the grille 65. Preferably, as described later (FIG. 12), a plurality of spaced-apart spacer posts project downwardly from the inside face of the top wall 20 of the ventilator chamber 3 to engage the inner ring 66 of the grille 65 to keep the filter 5 evenly spaced away from the top wall 20.

Figure 12:
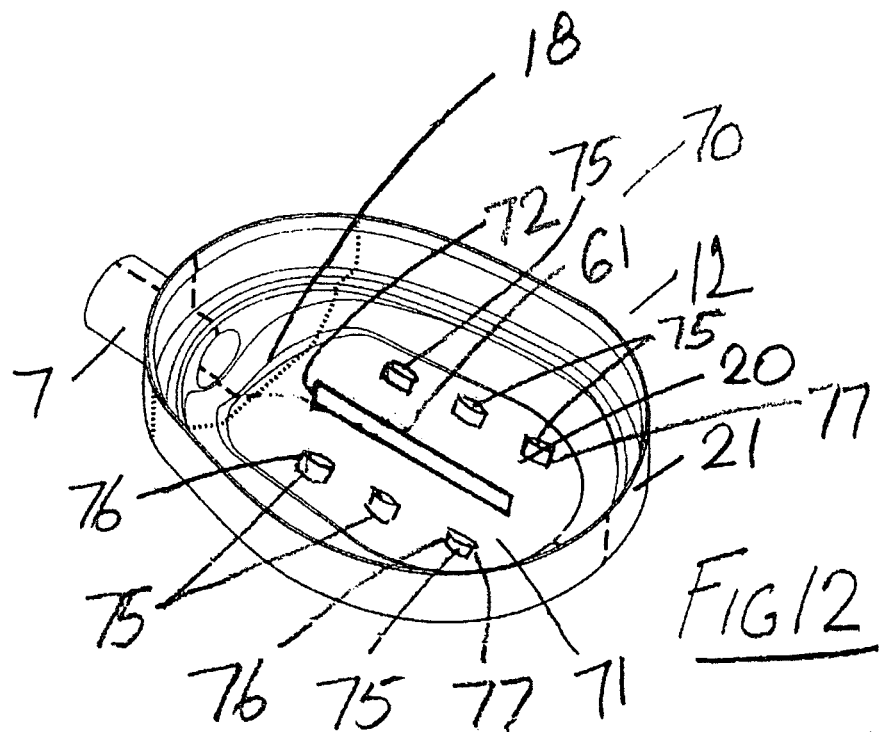
FIG. 12 is a perspective view of a ventilator chamber housing forming portion of a sedation device according to the invention.

Referring now to FIG. 12, there is shown another ventilator chamber housing 70 according to the invention. Parts similar to those described previously are assigned the same reference numerals. In this case, a central air distribution fin 61 projects inwardly from an inner face 71 of the top wall 20. A leading edge 72 and a trailing edge 73 of the air distribution fin are pointed. Also, a plurality of spaced-apart spacer posts 75 project inwardly from the inner face 71 of the top wall 20, arranged in rows on either side of the fin 61, and are engagable with the inner ring 66 of the grille 65 to maintain the grille 65 evenly spaced away from the inner face 71 of the top wall 20. Each spacer post 75 has a pointed leading edge 76 facing the inlet port 7, preferably the opposite or trailing edge 77 also being pointed.

Figure 13:
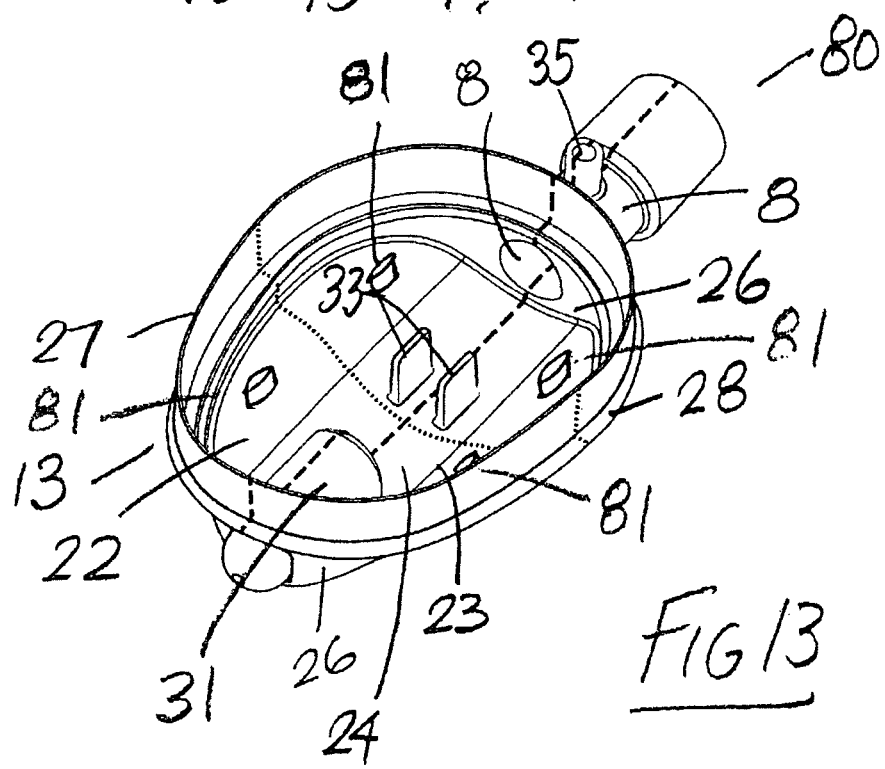
FIG. 13 is a perspective view of an evaporator chamber housing forming portion of a sedation device according to the invention.

FIG. 13 shows another evaporator chamber housing 80 according to the invention. Parts similar to those described previously have been assigned the same reference numerals. In this case, a plurality of spaced-apart spacer posts 81 project inwardly from the bottom wall 22 to keep the filter 5 spaced away from the bottom wall 22. These spacer posts 81 have pointed edges facing the direction of airflow through the evaporator chamber and are arranged in rows on either side of the central channel 24.

A second grille 65 may be provided for mounting in the evaporator chamber 4 against a lower surface 17 of the filter 5 to keep the filter 5 spaced away from the bottom wall 22 and being engaged and urged against the filter 5 by the support posts 33 and spacer posts 81.

Advantageously the sedation device of the invention functions effectively across a range of internal volumes, ideally between 30 ml and 110 ml, and preferably in the range 30 ml-70 ml, with minimal variation in pressure drop and sedative reflection efficiency.

While in the embodiments described, the inlet and outlet ports are disposed at opposite sides of the housing which is the preferred arrangement, other arrangements of the inlet port and outlet port are possible. Whichever arrangement is used, it is desirable to provide a smooth flow of air across the surface of the filter 5.

While an ovoid housing has been shown in the examples given, other shapes of housing are possible, such as an elliptical housing for example. Where an ovoid housing is used, the inlet port could be provided at either a narrow end, or a wide end of the housing and likewise the outlet port could be positioned at either a narrow end, or a wide end of the housing.

While the filter and the inlet port and the outlet port are parallel in the embodiments, the inlet port and/or the outlet port may be angled somewhat, providing that smooth air delivery across the surface of the filter is maintained.

It will be appreciated that the sedation device according to the invention provides a device that can be inserted into the ventilator circuit between a patient and a ventilator that is capable of delivering volatile sedative safely and cost-effectively to the patient. The sedation system of the invention delivers, conserves and reflects volatile sedative as efficiently as an anaesthesia machine, but at a fraction of the cost. The efficiency of the sedation device also means there is minimal waste of sedative, and any waste arising can easily be directed into a suitable scavenging unit. Conveniently the sedation device of the invention enables the use of volatile sedatives in ICU and other settings at relatively modest cost.

It will be appreciated that features of the various embodiments described herein may be combined in a sedation device according to this invention.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiments hereinbefore described which may be varied in both construction and detail within the scope of the appended claims.

What is claimed is:

1. A sedation device comprising:
    a housing having an internal volume of between 30 ml and 110 ml, the housing having a ventilator chamber and an associated juxtaposed evaporator chamber communicating with the ventilator chamber;
    a filter mounted between the ventilator chamber and the evaporator chamber forming a common gas-permeable dividing wall between the ventilator chamber and the evaporator chamber, the ventilator chamber having an inlet port for connection to a ventilator, the evaporator chamber having an outlet port for connection to a patient breathing tube; and
    an evaporator mounted within the evaporator chamber; wherein:
        the inlet port is mounted at a side of the ventilator chamber and is positioned to direct air across a surface of the filter in the ventilator chamber, and there is provided an air deflector ramp mounted within the ventilator chamber, the air deflector ramp associated with and adjacent the inlet port, the air deflector ramp extending across the inlet port and spaced-apart therefrom, the air deflector ramp being angled relative to the inlet port and flaring outwardly away from the inlet port to direct incoming air from the inlet port inwardly from the inlet port towards the filter and outwardly from the inlet port across a surface of the filter;
        an elongate air distribution fin is mounted within the ventilator chamber on an outer wall of the ventilator chamber in alignment with the inlet port at an inner end of the air deflector ramp and extending away from the air deflector ramp, the air distribution fin being perpendicular to the outer wall and centrally located on the outer wall in alignment with the inlet port, the air distribution fin having a pointed leading edge facing the inlet port;
        the air deflector ramp extends for between 20% and 35% of the length of the ventilator chamber, and a width of an outlet end of the air deflector ramp is between 50% and 75% of the maximum width of the ventilator chamber.

2. The sedation device as claimed in claim 1, wherein the evaporator chamber has a concave outer wall portion forming an elongate channel within which the evaporator is mounted, the evaporator comprising an elongate porous rod, evaporator mounting supports within the evaporator chamber supporting the evaporator rod within the elongate channel spaced-apart from the concave outer wall portion and in alignment with the outlet port of the evaporator chamber.

3. The sedation device as claimed in claim 2, wherein the evaporator mounting supports are provided at opposite ends of the evaporator chamber.

4. The sedation device as claimed in claim 3, wherein one of said evaporator mounting supports is mounted at the outlet port.

5. The sedation device as claimed in claim 3, wherein one or more filter support posts are mounted within the evaporator chamber located between the mounting supports and projecting outwardly from the concave outer wall portion.

6. The sedation device as claimed in claim 5, wherein each filter support post has a pointed edge facing towards the outlet port.

7. The sedation device as claimed in claim 1, wherein the outlet port is mounted at a side of the evaporator chamber and the outlet port is positioned to draw air across a surface of the filter in the evaporator chamber.

8. The sedation device as claimed in claim 1, wherein the ventilator chamber flares outwardly of the air deflector ramp.

9. The sedation device as claimed in claim 1, wherein the evaporator chamber has a side wall extending outwardly from the filter with the concave outer wall portion at an outer end of the side wall.

10. The sedation device as claimed in claim 9, wherein the side wall is tapered between opposite ends of the evaporator chamber, the outlet port being mounted at a wider end of the evaporator chamber.

11. The sedation device as claimed in claim 1, wherein a filter retaining grille is mounted in the ventilator chamber against the surface of the filter and at least one spacer element extends outwardly from an outer wall of the ventilator chamber to engage the grille and urge the grille away from the outer wall against the surface of the filter.

12. The sedation device as claimed in claim 11, wherein the spacer element comprises a plurality of spaced-apart spacer posts.

13. The sedation device as claimed in claim 12, wherein each spacer post has a pointed leading edge facing the inlet port.

14. The sedation device as claimed in claim 1, wherein the housing is ovoid.

15. The sedation device as claimed in claim 1, wherein the housing is elliptical.

16. The sedation device as claimed in claim 1, wherein the housing has an internal volume of about 50 ml.

17. A sedation device comprising:

a housing having an internal volume of between 30 ml and 110 ml, the housing having a ventilator chamber and an associated juxtaposed evaporator chamber communicating with the ventilator chamber;

a filter mounted between the ventilator chamber and the evaporator chamber forming a common gas-permeable dividing wall between the ventilator chamber and the evaporator chamber, the ventilator chamber having an inlet port for connection to a ventilator, the evaporator chamber having an outlet port for connection to a patient breathing tube; and an evaporator mounted within the evaporator chamber; wherein:

the inlet port is mounted at a side of the ventilator chamber and is positioned to direct air across a surface of the filter in the ventilator chamber, and there is provided an air deflector ramp mounted within the ventilator chamber, the air deflector ramp associated with and adjacent the inlet port, the air deflector ramp extending across the inlet port and spaced-apart therefrom, the air deflector ramp being angled relative to the inlet port and flaring outwardly away from the inlet port to direct incoming air from the inlet port inwardly from the inlet port towards the filter and outwardly from the inlet port across a surface of the filter;

an elongate air distribution fin is mounted within the ventilator chamber on an outer wall of the ventilator chamber in alignment with the inlet port at an inner end of the air deflector ramp and extending away from the air deflector ramp, the air distribution fin being perpendicular to the outer wall and centrally located on the outer wall in alignment with the inlet port, the air distribution fin having a pointed leading edge facing the inlet port.

18. A sedation device comprising:

a housing having an internal volume of between 30 ml and 110 ml, the housing having a ventilator chamber and an associated juxtaposed evaporator chamber communicating with the ventilator chamber;

a filter mounted between the ventilator chamber and the evaporator chamber forming a common gas-permeable dividing wall between the ventilator chamber and the evaporator chamber, the ventilator chamber having an inlet port for connection to a ventilator, the evaporator chamber having an outlet port for connection to a patient breathing tube; and an evaporator mounted within the evaporator chamber; wherein:

the inlet port is mounted at a side of the ventilator chamber and is positioned to direct air across a surface of the filter in the ventilator chamber, and there is provided an air deflector ramp mounted within the ventilator chamber, the air deflector ramp associated with and adjacent the inlet port, the air deflector ramp extending across the inlet port and spaced-apart therefrom, the air deflector ramp being angled relative to the inlet port and flaring outwardly away from the inlet port to direct incoming air from the inlet port inwardly from the inlet port towards the filter and outwardly from the inlet port across a surface of the filter;

an elongate air distribution fin is mounted within the ventilator chamber on an outer wall of the ventilator chamber in alignment with the inlet port at an inner end of the air deflector ramp and extending away from the air deflector ramp, the air distribution fin being perpendicular to the outer wall and centrally located on the outer wall in alignment with the inlet port, the air distribution fin having a pointed leading edge facing the inlet port;

a filter retaining grille is mounted in the ventilator chamber against the surface of the filter, the filter retaining grille having a pair of spaced-apart concentric ovoid rings, namely an inner ring and an outer ring, mounted on an axial spine with outwardly extending spaced-apart arms arranged thereon, the air distribution fin engaging against the central spine to keep the filter spaced away from the outer wall of the ventilator chamber.

\* \* \* \* \*